United States Patent
Undieh (10) Patent No.: US 9,593,360 B2
(45) Date of Patent: Mar. 14, 2017

(54) MEASUREMENT OF BRAIN CDP-DIACYLGLYCEROL SYNTHASE 1 ENZYME AND USES THEREOF

(71) Applicant: Ashiwel S Undieh, Ellicott City, MD (US)

(72) Inventor: Ashiwel S Undieh, Ellicott City, MD (US)

(*) Notice: Subject to any disclaimer, the term of this patent is extended or adjusted under 35 U.S.C. 154(b) by 620 days.

(21) Appl. No.: 13/626,051

(22) Filed: Sep. 25, 2012

(65) Prior Publication Data

US 2013/0022978 A1 Jan. 24, 2013

Related U.S. Application Data

(60) Continuation-in-part of application No. 12/804,534, filed on Jul. 23, 2010, now Pat. No. 8,278,296, which is a division of application No. 11/891,210, filed on Aug. 9, 2007, now Pat. No. 7,763,603.

(60) Provisional application No. 60/836,904, filed on Aug. 10, 2006.

(51) Int. Cl.
| | |
|---|---|
| *A61K 31/135* | (2006.01) |
| *A61K 31/445* | (2006.01) |
| *A61K 31/47* | (2006.01) |
| *C12Q 1/25* | (2006.01) |
| *A61K 31/55* | (2006.01) |
| *G01N 33/68* | (2006.01) |

(52) U.S. Cl.
CPC .............. *C12Q 1/25* (2013.01); *A61K 31/135* (2013.01); *A61K 31/445* (2013.01); *A61K 31/47* (2013.01); *A61K 31/55* (2013.01); *G01N 33/6896* (2013.01); *G01N 2800/304* (2013.01); *G01N 2800/52* (2013.01)

(58) Field of Classification Search
CPC .... A61K 31/135; A61K 31/445; A61K 31/47; C12Q 1/25
USPC ................ 514/217, 310, 321, 651, 654, 789
See application file for complete search history.

(56) References Cited

U.S. PATENT DOCUMENTS 6,211,171 B1* 4/2001 Sawynok et al. ........ 514/211.13
2008/0039443 A1 2/2008 Tyeryar

OTHER PUBLICATIONS

Tyerar, K. [Diverse Antidepressants Modulate One or More Components of Phosphoinositide Signaling Cascades in Depression-Relevant Brain Regions]. Program No. 306.5. 2002 Neuroscience Meeting Planner. Orlando, FL: Society for Neuroscience, 2002. Online.*
Volta, M. et al. Identification and characterization of CDS2, a mammalian homolog of the *Drosophila* CDP-diacylglycerol synthase gene. Genomics 1999; vol. 55: pp. 68-77; abstract.
Weeks, R. et al. Isolation and expression of an isoform of human CDP-diacylglycerol synthase cDNA. DNA Cell Biol. 1997; vol. 16: pp. 281-289; abstract.

* cited by examiner

*Primary Examiner* — Sahar Javanmard
(74) *Attorney, Agent, or Firm* — Benjamin Aaron Adler (57) ABSTRACT

Provided herein are methods of diagnosing depressive disorders in a subject by comparing a CDP-diacylglycerol synthase 1 enzyme activity or expression level to enzyme activity or expression level of CDP-diacylglycerol synthase 1 in a control subject. Also herein are methods of predicting therapeutic efficacy of an antidepressant drug in a subject with depressive disorders by monitoring enzyme activity or expression level of CDP-diacylglycerol synthase 1 in the subject. Further provided herein are methods of identifying a compound effective to treat or alleviate the symptoms of depression by monitoring enzyme activity or expression level of CDP-diacylglycerol synthase 1 in a tissue. Further provided are kits for diagnosing depressive disorders.

8 Claims, 2 Drawing Sheets

CDS2 Ab in Brain
(Predicted Mr ~51 kD)

Cb T   Cb T   Cb T
Pre     B1      B2

FIG. 1A

CDS1 Ab in Brain
(Predicted Mr ~65 kD)

Cb T   Cb T   Cb T
Pre     B1      B2

FIG. 1B

CDS1 Ab in Brain
(Predicted Mr ~65 kD)

H0 H1 H2   H0 H1 H2
   Pre          B2p

SEQUENCE LISTING

```
<160> NUMBER OF SEQ ID NOS: 11

<210> SEQ ID NO 1
<211> LENGTH: 23
<212> TYPE: DNA
<213> ORGANISM: Artificial Sequence
<220> FEATURE:
<223> OTHER INFORMATION: forward primer for human CDP-diacylglycerol
      synthase 1

<400> SEQUENCE: 1
ctggtttatc ttcaaggtgg aaa                                            23

<210> SEQ ID NO 2
<211> LENGTH: 20
<212> TYPE: DNA
<213> ORGANISM: Artificial Sequence
<220> FEATURE:
<223> OTHER INFORMATION: reverse primer for human CDP-diacylglycerol
      synthase 1
```

-continued

<400> SEQUENCE: 2
ttcacttgga tgcccagaac                                        20

<210> SEQ ID NO 3
<211> LENGTH: 20
<212> TYPE: DNA
<213> ORGANISM: Artificial Sequence
<220> FEATURE:
<223> OTHER INFORMATION: probe for human CDP-diacylglycerol synthase 1

<400> SEQUENCE: 3
cttcatgctg atgcttcttg                                        20

<210> SEQ ID NO 4
<211> LENGTH: 25
<212> TYPE: DNA
<213> ORGANISM: Artificial Sequence
<220> FEATURE:
<223> OTHER INFORMATION: forward primer for human CDP-diacylglycerol
      synthase 2

<400> SEQUENCE: 4
cctatttgaa ggaatgatct ggttc                                  25

<210> SEQ ID NO 5
<211> LENGTH: 19
<212> TYPE: DNA
<213> ORGANISM: Artificial Sequence
<220> FEATURE:
<223> OTHER INFORMATION: reverse primer for human CDP-diacylglycerol
      synthase 2

<400> SEQUENCE: 5
ggccatgatg tcattacag                                         19

<210> SEQ ID NO 6
<211> LENGTH: 19
<212> TYPE: DNA
<213> ORGANISM: Artificial Sequence
<220> FEATURE:
<223> OTHER INFORMATION: probe for human CDP-diacylglycerol synthase 2

<400> SEQUENCE: 6
cccatatctt gtgtgatct                                         19

<210> SEQ ID NO 7
<211> LENGTH: 21
<212> TYPE: DNA
<213> ORGANISM: Artificial Sequence
<220> FEATURE:
<223> OTHER INFORMATION: forward primer for GAPDH

<400> SEQUENCE: 7
gcctcaagat catcagcaat g                                      21

<210> SEQ ID NO 8
<211> LENGTH: 22
<212> TYPE: DNA
<213> ORGANISM: Artificial Sequence
<220> FEATURE:
<223> OTHER INFORMATION: reverse primer for GAPDH

<400> SEQUENCE: 8
cttccacgat accaaagttg tc                                     22

```
<210> SEQ ID NO 9
<211> LENGTH: 17
<212> TYPE: DNA
<213> ORGANISM: Artificial Sequence
<220> FEATURE:
<223> OTHER INFORMATION: probe primer for GAPDH

<400> SEQUENCE: 9
gccaaggtca tccatga                                                  17

<210> SEQ ID NO 10
<211> LENGTH: 16
<212> TYPE: PRT
<213> ORGANISM: Artificial Sequence
<220> FEATURE:
<223> OTHER INFORMATION: antigenic epitope used to develop antibody for
      human CDP-diacylglycerol synthase 1

<400> SEQUENCE: 10

Cys Asp Asp Arg Tyr Gly Asp Leu Asp Ser Arg Thr Asp Ser Asp Ile
1               5                   10                  15

<210> SEQ ID NO 11
<211> LENGTH: 16
<212> TYPE: PRT
<213> ORGANISM: Artificial Sequence
<220> FEATURE:
<223> OTHER INFORMATION: antigenic epitope used to develop antibody for
      human CDP-diacylglycerol synthase 2

<400> SEQUENCE: 11

Cys Asp Lys Glu Ser Glu Ser Glu Ala Lys Val Asp Gly Glu Thr Ala
1               5                   10                  15
```

MEASUREMENT OF BRAIN CDP-DIACYLGLYCEROL SYNTHASE 1 ENZYME AND USES THEREOF

CROSS-REFERENCE TO RELATED APPLICATION

This continuation in part patent application claims benefit of priority under 35 U.S.C. §120 of pending divisional application U.S. Ser. No. 12/804,534, filed Jul. 23, 2010 which claims benefit of priority under 35 U.S.C. §120 of nonprovisional application U.S. Ser. No. 11/891,210, filed Aug. 9, 2007, now U.S. Pat. No. 7,763,603 which claims benefit of priority under 35 U.S.C. §119(e) of provisional application U.S. Ser. No. 60/836,904, filed Aug. 10, 2006, the entirety of both of which are hereby incorporated by reference.

FEDERAL FUNDING LEGEND

This invention was produced in part using funds obtained through the National Institutes of Health NIDA Grant No. DA017614. Consequently, the federal government has certain rights in this invention.

BACKGROUND OF THE INVENTION

Field of the Invention

The present invention relates generally to the fields of psychiatric medicine and pharmacology. More specifically, the present invention provides methods to diagnosis and prognosis of depressive disorders by targeting specific signaling molecules.

Description of the Related Art

Major depression is a serious mood disorder that annually afflicts millions of people worldwide (1-3). Despite years of research, the biological causes and pathological mechanisms of major depressive disorder are unclear. Further, while treatments are available for managing the disease symptoms, efforts to develop safer and more effective medications are hampered because the mechanism of action of antidepressants is not well understood (4-5).

It is well known, however, that antidepressants with differing chemical and clinical properties can increase the synaptic levels of the neurotransmitters, i.e., serotonin, norepinephrine, and/or dopamine, in discrete brain regions (6-7). The monoamine transmitters may then activate their cognate postsynaptic receptors and modulate the activities of downstream signaling cascades to possibly produce the antidepressive effect. It remains to be clarified, however, which among the numerous postsynaptic receptors and signaling components may be involved in the mode of action of antidepressants (5, 8-9).

Receptors for the monoamine neurotransmitters are coupled to diverse signaling pathways, including adenylyl cyclase, phospholipases, and MAP kinase pathways (10-13). Aspects of each of these signaling systems have been investigated as potential downstream targets of antidepressive mechanisms (8, 14-15). As examples, acute or chronic treatment with various antidepressant compounds can lead to changes in basal or drug-induced activities of brain adenylyl cyclase (16-19), phospholipase A2, CREB, inositol phosphates (IPs), phosphoinositide-specific phospholipase C (PLC), phosphatidylinositides, protein kinase C (PKC), extracellular signal regulated kinase, ion channels, neurotrophins, and neuropeptides. Antidepressants can also enhance neurogenesis, modulate neuronal excitability, and alter the gene expression of various signaling components including neurotransmitter transporters, receptors, transducers, and effectors (39-46). While these observations indicate that changes in postsynaptic signaling cascades may constitute an integral component in the mechanisms that underlie depression or its treatment with antidepressant medications, no signaling cascade has been identified that explains the functional and clinical data.

The depression or antidepressant-related phosphoinositide observations have been corroborated by clinical studies showing that depressed persons have reduced cortical levels of the phosphoinositide precursor myo-inositol (47-48). Moreover, oral ingestion of pharmacological doses of myo-inositol may elicit antidepressive responses in rodents and enhance the recovery of clinically depressed patients (49-51). Consistent with these findings, chronic administration of antidepressant agents has been associated with increased levels of phosphatidylinositol (PI), phosphatidylinositol phosphate (PIP), and phosphatidylinositol bisphosphate (PIP2) in human platelets (24,27). These observations support the notion that alterations in the phosphoinositide signaling pathway may be implicated in the pathophysiology of depression and/or the mode of action of antidepressant agents (5,26,52).

Several studies have hinted at links between the phosphoinositide system, PKC activity, and depression (28-30). However, these studies have not assessed the status of diacylglycerol production or metabolism as a potential target of disease pathology or pharmacological treatment. Diacylglycerol signaling is important as it is the endogenous regulator of PKC activity (Nishizuka, 1992). Among PLC-coupled receptors, however, significant differences exist in the ability of receptor activation to generate diacylglycerol, relative to IP, from receptor-mediated phospholipid hydrolysis (53-54).

It is recognized, therefore, to the extent that PI signaling or PKC activity may be involved in antidepressant drug action, that there is a significant need in the art for improvements in the area of treating depression with antidepressant agents that target cellular CDP-diacylglycerol. Specifically, the prior art is deficient in methods of screening for novel compounds that increase cellular CDP-diacylglycerol and methods of diagnosing and treating depression using the same. The present invention fulfills this long-standing need and desire in the art.

SUMMARY OF THE INVENTION

It is an object of the present invention to demonstrate that the protein and/or mRNA levels of two CDP-diacylglycerol synthase (CDS) isoforms—CDS1 and CDS2—are altered in postmortem forebrain tissues of depression subjects.

It is a further object of the present invention to demonstrate that there are measurable levels of CDS isozymes in circulating peripheral blood.

The present invention is directed, in part, to a method of diagnosing a depressive disorder in a test subject. The method comprises determining CDP-diacylglycerol synthase 1 enzyme activity or expression level in the test subject and comparing the enzyme activity or CDP-diacylglycerol synthase 1 expression level to enzyme activity or expression level of CDP-diacylglycerol synthase 1 in a control subject. A statistically lower enzyme activity or expression level in the test subject indicates the test subject has a depressive disorder.

The present invention is directed to a related method of predicting therapeutic efficacy of an antidepressant drug in a subject with a depressive disorder. The method comprises determining CDP-diacylglycerol synthase 1 enzyme activity or expression level of CDP-diacylglycerol synthase 1 in the subject, administering an antidepressant drug to the subject and monitoring CDP-diacylglycerol synthase 1 enzyme activity or expression level of CDP-diacylglycerol synthase 1 in the subject after administration of the antidepressant drug to the subject. A statistically higher CDP-diacylglycerol synthase 1 enzyme activity or CDP-diacylglycerol synthase 1 expression level after administration of the antidepressant drug to the subject indicates that the antidepressant drug has therapeutic efficacy for the subject.

The present invention is directed further yet to a method of identifying a compound effective to treat or alleviate the symptoms of depression. The method comprises determining CDP-diacylglycerol synthase 1 enzyme activity or expression level of CDP-diacylglycerol synthase 1 in a tissue, contacting the tissue with a potential antidepressant compound and determining the level of CDP-diacylglycerol synthase 1 enzyme activity or expression level of CDP-diacylglycerol synthase 1 in the tissue after the contact. A statistically higher CDP-diacylglycerol synthase 1 enzyme activity or CDP-diacylglycerol synthase 1 expression level in the tissue after treatment with the compound indicates that the compound has an antidepressant effect.

The present invention is directed further still to a kit for diagnosing a depressive disorder. The kit comprises an antibody to CDP-diacylglycerol synthase 1 protein, an antibody to CDP-diacylglycerol synthase 2 protein and instructions for measurement of the proteins for the diagnosis of the depressive disorder.

The present invention is directed further still to a kit for diagnosing a depressive disorder. The kit comprises forward and reverse primers for CDP-diacylglycerol synthase 1 gene, a probe that hybridizes with CDP-diacylglycerol synthase 1 gene, forward and reverse primers for CDP-diacylglycerol synthase 2 gene, a probe that hybridizes with CDP-diacylglycerol synthase 2 gene and instructions for measurement of said genes for the diagnosis of said depressive disorder.

Other and further aspects, features and advantages of the present invention will be apparent from the following description of the presently preferred embodiments of the invention. These embodiments are given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention are briefly summarized. The above may be better understood by reference to certain embodiments thereof which are illustrated in the appended drawings. These drawings form a part of the specification. It is to be noted; however, that the appended drawings illustrate preferred embodiments of the invention and therefore are not to be considered limiting in their scope.

DETAILED DESCRIPTION OF THE INVENTION

Definitions

As used herein, the term "a" or "an", when used in conjunction with the term "comprising" in the claims and/or the specification may mean "one", but it is also consistent with the meaning of "one or more", "at least one", and "one or more than one". Some embodiments of the invention may consist of or consist essentially of one or more elements, method steps, and/or methods of the invention. It is contemplated that any method, compound, drug, or composition described herein can be implemented with respect to any other method, compound, drug, or composition described herein.

As used herein, the term "or" in the claims is used to mean "and/or" unless explicitly indicated to refer to alternatives only or the alternatives are mutually exclusive, although the disclosure supports a definition that refers to only alternatives and "and/or".

As used herein, the term "antidepressant drug or agent" refers to known compounds exhibiting an antidepressive effect or antidepressant effect on a subject having depression or a depressive disorder or mood disorder. Antidepressants may be, but not limited to, the tricyclic antidepressants, e.g., desipramine and imipramine, the selective serotonin reuptake inhibitors, e.g., fluoxetine and paroxetine, the atypical antidepressants, e.g., maprotiline and nomifensine, or de novo compounds SKF83959 or 6-chloro-7,8-dihydroxy-3-methyl-1-(3-methylphenyl)-2,3,4,5-tetrahydro-1H-3-benzazepine (55) and SKF38393 or (+/−)-1-phenyl-2,3,4,5-tetrahydro-(1H)-3-benzazepine-7,8-diol (56).

As used herein, the term "potential antidepressant compound" or "screened antidepressant compound" refers to a compound having, although not limited to, a similarity in structure, such as a derivative or analog, to a known antidepressant drug or agent" and/or a therapeutic ability to at least increase accumulation of cellular CDP-diacyglycerol and inositol phosphate and enhance synthesis of inositol phospholipids in brain tissue and/or blood cells.

As used herein, the term "structural derivative" refers to a change to the structure of an original compound that conserves the functional aspects, i.e., biological activity, efficacy, and the like, of the original compound. For example, an original compound may be SKF83959 and a structural derivative may include an addition and/or a modification of the original benzazepine structure, such as changing halogen substituents, oxidation state, hydration, salt counterions, and the like.

As used herein, the term "CDP-DG/IP ratio" refers to the relative value of an index which is the quotient of a level of cellular CDP-diacylglycerol divided by a level of inositol phosphate in a tissue or cell or tissue cultures thereof, e.g., a mammalian brain tissue or blood platelets, a human brain tissue or blood platelets, or other cells or tissues having the ability to metabolize CDP-diacylglycerol and phosphoinositides. Levels may be determined, including but are not limited to, using molar concentration or a radiolabel.

As used herein, the term "contacting" refers to any suitable method of bringing an antidepressant drug or agent or potential antidepressant compound into contact with a tissue or cell, e.g., a mammalian brain tissue or blood platelets or other blood cells, a human brain tissue, blood platelets or other blood cells, or other cells or tissues having the ability to metabolize CDP-diacylglycerol and phosphoinositides. In vitro or ex vivo this is achieved by exposing the tissue in a cell or tissue culture to the anti-depressive agent or potential antidepressive compound in a suitable medium. For in vivo applications, any appropriately known method of administration is suitable.

As used herein, the terms "effective amount" or "pharmacologically effective amount" or "therapeutically effective amount" are interchangeable and refer to an amount that results in an improvement or remediation of the symptoms of the depressive disorder or condition. The amount is sufficient to detectably and repeatedly to ameliorate, reduce, minimize, or limit the extent of the depressive disorder or condition or the symptoms thereof. Those of skill in the art understand that the effective amount may improve the patient's or subject's condition, but may not be a complete cure of the depressive disorder and/or condition.

As used herein, the term "depressive disorder" or "mood disorder" refers to clinical depression, major depression, unipolar depression, reactive depression, endogenous depression, dysthymia, or bipolar disorder. Major depression, which is also known as clinical depression or unipolar depression, is a mood disorder in which feelings of sadness, loss, anger, or frustration interfere with everyday life for weeks or longer. Bipolar disorder, also known as manic-depressive disorder, is a mood disorder that causes radical emotional changes and mood swings, from manic, restless highs to depressive, listless lows. Reactive depression is a usually transient depression that is precipitated by a stressful life event or other environmental factor. Endogenous depression is caused by an intrinsic biological or somatic process rather than an environmental influence, in contrast to a reactive depression. Dysthymic depression is a mood disorder with mild and chronic depressive symptoms that are present most of the day, more days than not, for a period of at least two years.

As used herein, the term "subject" refers to any target of the treatment, preferably a mammal, more preferably a human.

In one embodiment of the present invention, there is provided a method of identifying a compound effective to treat or alleviate the symptoms of depression, comprising contacting a tissue having a CDP-diacylglycerol and phosphoinositides metabolic activity with a potential antidepressant compound; determining a level of CDP-diacylglycerol (CDP-DG) and a level of inositide (inositol phosphate and/or phosphoinositide) in the tissue after contact therewith; and comparing an index value that is a ratio of CDP-diacylglycerol to inositide in test tissue to a control index value, wherein a higher CDP-DG/Inositide index value in tissue treated with the compound indicates the potential compound has an antidepressant effect.

Further to this embodiment, the method comprises designing the potential antidepressive compound prior to screening, where the design is based on the structure of a tricyclic antidepressant, a selective serotonin reuptake inhibitor or an atypical antidepressant or on a structure of a compound structurally dissimilar thereto exhibiting an antidepressant effect or synthesizing a potential compound de novo. Examples of a tricyclic antidepressant is desipramine or imipramine. Examples of a selective serotonin reuptake inhibitor are fluoxetine or paroxetine. Examples of an atypical antidepressant are maprotiline or nomifensine. Other atypical antidepressants may be SKF83959, or SKF38393 or a structural derivative thereof. In another further embodiment the method comprises treating a subject having a depressive disorder with the compound screened by the method.

In another embodiment of the present invention, there is provided a compound screened by the method described supra. In a related embodiment there is provided a synthetic antidepressant compound effective to increase production of CDP-diacylglycerol and synthesis of inositide in a depression-relevant brain tissue or blood tissue upon contact therewith. In both embodiments, the screened compound and the synthetic antidepressant compound may be an analog or derivative of a tricyclic antidepressant, a selective serotonin reuptake inhibitor or an atypical antidepressant. Examples of these antidepressants are described supra. In another related embodiment there is provided a synthetic compound effective to increase CDP-diacylglycerol synthase activity in a depression-relevant brain tissue, blood cells or other body tissue upon contact therewith.

In yet another embodiment of the present invention, there is provided a method of treating a depressive disorder in a subject, comprising administering one or more of the screened compounds described supra to the subject, thereby treating the antidepressive disorder. Further to this embodiment the method comprises administering one or more other known antidepressant drugs or other known compounds effective to increase an CDP-DG/Inositide index. The antidepressant drugs may be a tricyclic antidepressant, a selective serotonin reuptake inhibitor or an atypical antidepressant with specific examples thereof as described supra. The other known compound is SKF83959 or SKF38393 or a structural derivative thereof. Examples of the depressive disorder include but are not limited major depression, unipolar depression, bipolar depression, reactive depression, endogenous depression or dysthymic disorder.

In another further embodiment the method comprises diagnosing the depressive disorder in a subject prior to treatment thereof. In this further embodiment diagnosing the depressive disorder comprises determining a level of CDP-diacylglycerol and a level of inositide in the subject; and comparing an index value that is a ratio of CDP-diacylglycerol to inositide in the subject to a control index value, wherein a lower CDP-DG/Inositide index value indicates the subject has a depressive disorder.

In yet another further embodiment, the method comprises determining a combination of the screened antidepressive compounds, the other antidepressant drugs or a combination thereof having maximum therapeutic efficacy against the depressive disorder. Determining the combination of antidepressant drugs comprises administering a first selected combination of antidepressants to the subject; determining a first index value that is a level of CDP-diacylglycerol (CDP-DG) and of inositide in the subject after administration of the antidepressant combination; and comparing the first index value to the CDP-DG/Inositide index values of subsequently and individually administered combinations of other antidepressants; wherein the combination having the highest CDP-DG index correlates to a maximum therapeutic efficacy.

In a related embodiment, there is provided a method of treating depression in a subject, comprising administering a CDP-diacylglycerol-increasing amount of a compound to the subject, where the compound increases CDP-diacylglycerol metabolism in the subject, thereby treating the depression. Representative examples of the compound are maprotiline, nomifensine, SKF83959, SKF38393, or a structural derivatives thereof.

In yet another embodiment, there is provided a method of diagnosing a depressive disorder in a subject, comprising determining a basal CDP-DG/Inositide index that is the ratio of a level of CDP-diacylglycerol to a level of inositide in the subject; and comparing the basal CDP-DG/Inositide index to a control CDP-Inositide index, where a lower basal CDP-DG/Inositide index indicates the subject has a depressive disorder. In this related embodiment the diagnosis may be predictive of the onset of a depressive disorder. The depressive disorder may be as described infra.

In still another embodiment of the present invention there is provided method of predicting therapeutic efficacy of an antidepressant drug regimen in a subject having a depressive disorder, comprising administering a first selected drug regimen that is a combination of antidepressant drugs to the subject; determining a first CDP-DG/Inositide index value that is the ratio of a level of CDP-diacylglycerol (CDP-DG) to a level of inositide in the subject after administration; comparing the first index value to the CDP-DG/Inositide index values of subsequently and individually administered combinations of other selected antidepressants; wherein an ordering of the relative index values correlates to therapeutic efficacy of the drug regimen. In this embodiment, the combination of antidepressant drugs may comprise a tricyclic antidepressant(s), a selective serotonin reuptake inhibitor(s) or an atypical antidepressant(s) or derivatives or analogs thereof or a novel synthetic antidepressant compound designed de novo that increases production of CDP-diacylglycerol and synthesis of inositol in a depression-relevant brain tissue or blood cells or other body tissue. The examples of a tricyclic antidepressant, a selective serotonin reuptake inhibitor and an atypical antidepressant are as described supra. Also, the depressive disorder may be as described supra.

The present invention demonstrates that antidepressants belonging to diverse chemical and pharmacological classes acutely increase the formation of CDP-diacylglycerol (CDP-DG), a metabolic derivative of diacylglycerol, which effect may translate to enhanced resynthesis of the phosphatidylinositides. Phosphatidylinositides are metabolically used either as substrates for PLC or as precursors to the phosphatidylinositol-3-kinase (PI-3-K)/Akt signaling cascade. It is contemplated, therefore, that an acute molecular action of antidepressant agents that facilitates the conservation or supplementation of cellular phosphatidylinositides may contribute to the therapeutic mechanism of these medications in depression-relevant brain regions.

It is also contemplated that known antidepressants may exert tandem neurochemical effects by increasing synaptic monoamine concentrations and by producing phosphoinositide substrates used in 5HT2 receptor signaling. This combination of actions may constitute the mechanism of at least the acute behavioral effects of antidepressant medications and, thereby, may implicate aberrant phospholipid signaling in the neuropathology of depressive disorder.

Thus, provided herein is a method of screening for potential antidepressant compounds. Potential antidepressant agents are distinguished from other compounds that enhance phosphoinositide signaling by the relative value of the CDP-DG/Inositide index. An increase in the CDP-DG/Inositide index compared to a control index is indicative that the potential antidepressant compound may exhibit antidepressant effects by at least increasing cellular CDP-diacylglycerol in a subject with a depressive or mood disorder. Cellular levels of CDP-diacylglycerol and inositide may be determined in brain tissue, blood platelets or other blood cells, cultured cells or combination of tissues in the presence and absence of potential antidepressant compounds using assay methods known and standard in the art.

As such, the antidepressant compounds identified by the screening method also are provided. It is contemplated that these screened antidepressant compounds may be derivatives or analogs of known antidepressant drugs or agents as described herein. Alternatively, the antidepressant compounds may have a novel synthetic structure designed de novo using standard methods of chemical design known in the art, for example, but not limited to, computer aided drug design.

Compositions, Pharmaceutical Formulations and Methods of Treating

The present invention also contemplates therapeutic or treatment methods employing compositions comprising the screened antidepressant compounds disclosed herein, that is, compositions comprising the known antidepressant drugs and/or the screened antidepressant compounds provided herein. Preferably, these compositions include pharmaceutical compositions comprising a therapeutically effective amount of one or more of the active compounds or substances along with conventional non-toxic, physiologically or pharmaceutically acceptable carriers or vehicles suitable for the method of administration.

Treatment methods will involve treating an individual with an effective amount of a composition containing the screened antidepressant compound and/or known antidepressant drug or related compounds thereof. More specifically, it is envisioned that the treatment with the antidepressant compounds and/or antidepressant drugs or related-compounds thereof will increase production of CDP-diacylglycerol and synthesis of inositol phospholipids in depression-relevant brain tissues or blood platelets or other blood cells to produce a beneficial result in a depressive or mood disorder.

Thus, methods of diagnosing a depressive disorder in a subject, preferably a human, are provided. Brain, peripheral tissue, platelet or other blood cell levels of CDP-diacylglycerol are measured to aid diagnosis of an active or impending depressive episode. A determination of an abnormal CDP-diacylglycerol signaling in the subject may be indicative of a depressive or mood disorder. Therefore, the CDP-DG/Inositide index may be a useful diagnostic tool in the diagnosis of a depressive or mood disorder.

In addition, methods of treating a depressive or mood disorder in a subject are provided. A pharmacologically effective or therapeutically effective amount of one or more of the screened antidepressive compounds described herein or a pharmaceutical composition comprising the same is administered to the subject. Alternatively, treatment may comprise a combination of the screened antidepressive compound(s) and one or more known antidepressants or pharmaceutical compositions thereof. As such, treatment by, for example, but not limited to, atypical antidepressants or structural derivatives thereof provide a therapeutic effect of at least increasing CDP-diacylglycerol metabolism.

Further provided is a method of predicting the potential effectiveness of antidepressant combinations for various patients based on the basal CDP-DG/Inositide ratio of each patient. An increase in the CDP-DG/Inositide index compared to the basel index of current or novel antidepressant compounds may be predictive of antidepressant effects in a subject. A successful regimen may comprise a combination of the known tricyclic antidepressants, the known selective serotonin reuptake inhibitors and the known atypical antidepressants and/or the novel antidepressant compounds screened as described herein.

In still another embodiment of the present invention, there is provided a method of diagnosing a depressive disorder in a test subject. The method comprises determining CDP-diacylglycerol synthase 1 enzyme activity or CDP-diacylglycerol synthase 1 expression level in the test subject and comparing the enzyme activity or expression level to CDP-diacylglycerol synthase 1 enzyme activity or expression level of CDP-diacylglycerol synthase 1 in a control subject. A statistically lower enzyme activity or expression level in the test subject indicates the test subject has a depressive disorder. In this embodiment, the expression level is typically determined by measuring a CDP-diacylglycerol synthase 1 protein, a ratio of a CDP-diacylglycerol synthase 1 protein to a CDP-diacylglycerol synthase 2 protein, a CDP-diacylglycerol synthase 1 mRNA or a ratio of a CDP-diacylglycerol synthase 1 mRNA to a CDP-diacylglycerol synthase 2 mRNA. The enzyme activity or expression level of CDP-diacylglycerol synthase is typically determined in blood, brain tissue, testis tissue, eye tissue or smooth muscle tissue. M Examples of the depressive disorder include but are not limited to major depression, unipolar depression, bipolar depression, reactive depression, endogenous depression, or dysthymic disorder.

Further to this embodiment, a CDP-diacylglycerol synthase 1 protein level in the test subject that is about 75% or lower than a CDP-diacylglycerol synthase 1 protein level in the control subject typically indicates that the test subject has a depressive disorder. A CDP-diacylglycerol synthase 1 mRNA level in the test subject that is about 68% or lower than a CDP-diacylglycerol synthase 1 mRNA level in the control subject typically indicates that the test subject has a depressive disorder. A ratio of a CDP-diacylglycerol synthase 1 mRNA to a CDP-diacylglycerol synthase 2 mRNA in the test subject that is about 73% or lower than a ratio of a CDP-diacylglycerol synthase 1 mRNA to a CDP-diacylglycerol synthase 2 mRNA in the control subject typically indicates that the test subject has a depressive disorder.

In still another embodiment of the present invention, there is provided a method of predicting therapeutic efficacy of an antidepressant drug in a subject with a depressive disorder. The method comprises determining CDP-diacylglycerol synthase 1 enzyme activity or expression level of CDP-diacylglycerol synthase 1 in the subject, administering an antidepressant drug to the subject and monitoring enzyme activity or expression level of CDP-diacylglycerol synthase 1 in the subject after administration of the antidepressant drug to the subject. A statistically higher enzyme activity or expression level after administration of the antidepressant drug to the subject indicates that the antidepressant drug has therapeutic efficacy for the subject.

In this embodiment, examples of the antidepressant drug include but are not limited to a tricyclic antidepressant, a selective serotonin reuptake inhibitor, an atypical antidepressant or a synthetic antidepressant compound that increases an enzyme activity or expression level of a CDP-diacylglycerol synthase 1 in a depression-relevant brain tissue or blood platelets. A representative tricyclic antidepressant is desipramine or imipramine and a representative selective serotonin reuptake inhibitor is fluoxetine or paroxetine. Examples of the depressive disorder include but are not limited to major depression, unipolar depression, bipolar depression, reactive depression, endogenous depression, or dysthymic disorder. Further to this embodiment, the expression level is typically determined by measuring a CDP-diacylglycerol synthase 1 protein, a ratio of a CDP-diacylglycerol synthase 1 protein to a CDP-diacylglycerol synthase 2 protein, a CDP-diacylglycerol synthase 1 mRNA or a ratio of a CDP-diacylglycerol synthase 1 mRNA to a CDP-diacylglycerol synthase 2 mRNA. The CDP-diacylglycerol synthase 1 enzyme activity or expression level of CDPdiacylglycerol synthase is typically determined in blood, brain tissue, testis tissue, eye tissue or smooth muscle tissue.

In still another embodiment of the present invention, there is provided a method of identifying a compound effective to treat or alleviate the symptoms of depression. The method comprises determining level of enzyme activity or expression level of CDP-diacylglycerol synthase 1 in a tissue, contacting the tissue with a potential antidepressant compound and determining level of CDP-diacylglycerol synthase 1 enzyme activity or expression level of CDP-diacylglycerol synthase 1 in the tissue after the contact. A statistically higher enzyme activity or expression level in the tissue after treatment with the compound indicates that the compound has an antidepressant effect.

The present invention is directed further still to a kit for diagnosing a depressive disorder. The kit comprises an antibody to CDP-diacylglycerol synthase 1 protein, an antibody to CDP-diacylglycerol synthase 2 protein and instructions for measurement of the proteins for the diagnosis of the depressive disorder.

The present invention is directed further still to a kit for diagnosing a depressive disorder. The kit comprises forward and reverse primers for CDP-diacylglycerol synthase 1 gene, a probe that hybridizes with CDP-diacylglycerol synthase 1 gene, forward and reverse primers for CDP-diacylglycerol synthase 2 gene, a probe that hybridizes with CDP-diacylglycerol synthase 2 gene and instructions for measurement of said genes for the diagnosis of said depressive disorder.

The following examples are given for the purpose of illustrating various embodiments of the invention and are not meant to limit the present invention in any fashion.

EXAMPLE 1

Animals

Male Sprague-Dawley rats, weighing between 225 g-300 g, were obtained from Zivic Laboratories (Zelienople, Pa.) and housed in climate-controlled facilities with a 12-h light/dark cycle for at least 3 days before use. The animals were caged in groups of three and allowed free access to food and water.

Drugs and Chemicals

Antidepressant compounds and buffer reagents were purchased from Sigma-Aldrich (St. Louis, Mo.). SKF38393 was from the NIMH Chemical Synthesis Program (NIMH, Bethesda, US). Nomifensine was first dissolved in 0.2% tartaric acid and SKF38393 in distilled water before either drug was diluted to use concentrations in assay buffer. Other drugs were prepared fresh in HEPES bicarbonate assay buffer (HBB) (57). Each experiment was performed on multiple occasions using fresh preparations of drugs. Protein was assayed by the Bradford method using BioRad protein assay reagents (BioRad, Hercules, Calif.).

Measurement of CDP-Diacylglycerol Accumulation

Accumulation of CDP-diacylglycerol was measured in brain slice preparations by taking advantage of the CTP-phosphatidate transfer reaction (58-60). Briefly, male Sprague-Dawley rats weighing between 225 and 300 g were rapidly decapitated and the brains removed and rinsed in calcium-free HBB (58,61). Brain regions of interest, including the hippocampus, prefrontal cortex and striatum, were quickly dissected out and 350 μm prisms prepared using a McIlwain tissue chopper (61). The slices were washed with calcium-free HBB and pre-incubated for 45 minutes at 37° C. Slice aliquots of approximately 300 μg protein then were incubated with 1.5 μCi of 5-[$^3$H]cytidine (20 Ci/mmol; American Radiolabeled Chemicals, St. Louis, Mo.) in order to generate an endogenous pool of radiolabeled cytidine triphosphate (CTP) for feeding into the CTP:phosphatidate transfer reaction (58).

Following addition of 5 mM LiCl, test drugs or buffer were added for a total volume of 250 μl and incubation continued for 60 or 90 min as indicated. Reactions were terminated by addition of 1.5 ml chloroform-methanol-1M HCl (100:200:1). Formed lipids were extracted by liquid partitioning in chloroform followed by centrifugation at 1000×g for 5 min to separate the liquid phases. Aliquots of the organic phase were transferred quantitatively into scintillation vials, dried at room temperature and redissolved in Biosafe scintillation cocktail. Radioactivity in this lipid fraction was determined by liquid scintillation spectrometry, and corresponds to [$^3$H]CDP-DG (54,58,62).

Measurement of Inositol Phospholipid Resynthesis

Brain tissues were prepared and were incubated as described above for assaying CDP-DG, except that 1.5 μCi of [$^3$H]inositol (20 Ci/mmol; American Radiolabeled Chemicals, St. Louis, Mo.) was used instead of [$^3$H]cytidine to label the slices. Following the labeling incubation, drugs were added and allowed to act for 60 or 90 min as indicated. Samples were extracted with chloroform-methanol-1M HCl (100:200:1), partitioned with chloroform into aqueous and organic phases, and aliquots of the organic phase dried and assessed for radioactivity that corresponded to the inositol phospholipids. It was not necessary to attempt to separate the multiple phosphorylated or isomeric forms of these phospholipids. Hence, the data potentially represent the mix of phosphatidylinositol, phosphatidylinositol-4-phosphate, and phosphatidylinositol 4,5-bisphosphate in any of their positional isomeric forms. Based on the levels of the phospholipids present at the start of drug treatment, a subsequent decrease is seen as depletion, whereas an increase in the [$^3$H]inositol-labeled pool of the phospholipids is considered to represent further phospholipid synthesis or resynthesis (59,63).

Measurement of Inositol Phosphate Accumulation

To measure the levels of IPs formed, tissues were treated exactly as in the PI synthesis assays described herein, including the use of [$^3$H]inositol for prelabeling of the PI pool. The 250 μl reactions were terminated by mixing the samples with 1.5 ml of chloroform-methanol-1 M HCl (100:200:1). Following chloroform-mediated partitioning of the extracts as described (57), aliquots of the aqueous phase were analyzed for the content of [$^3$H]IPs by Dowex anion exchange chromatography (57,61). An IP fraction was collected from the eluate and the solution converted into a gel by use of Scintisafe Gel (Fisher Scientific, Pittsburgh, Pa.). The amounts of IP-associated radioactivity in the samples were then measured by liquid scintillation spectrometry.

Forced Swim Test

The forced swim test (FST) was applied with some modifications. Rats were transferred to the testing room between 9:00-10:00 AM and allowed at least an hour before being placed individually into translucent polypropylene cylinders (46 cm tall×25 cm in diameter) containing 27 cm depth of water maintained at 25° C. (64-65). After 15 min in the water, the rats were removed, toweled, and allowed to dry in a warm environment before being returned to their home cage. This acclimation step was repeated after 24 h, with the exposure time reduced from 15 to 5 min. Preliminary testing showed that the double acclimation exposure produced more consistent results among animals in each test group (lower variability) than the conventional single acclimation.

During the second acclimation exposure, the duration of immobility was recorded for each animal. While the initial intent was to eliminate animals that did not attain immobility within 5 min, in practice all animals used in the present experiments passed this test at the second acclimation session. To adjudge that a rat had become immobile, the animal had to float passively in the water in a slightly hunched, but upright position, making only minimal movements necessary to keep its head above the water (65-66).

On the third day when animals were to undergo experimental assessment, saline or the indicated antidepressant agents were administered i.p. at 3 h and at 1 h before behavioral testing. The drugs were dissolved in distilled-deionized water and diluted in saline. Control subjects received 0.9% saline. Drugs were freshly made before use and injected in a constant volume of 1 ml/kg except for fluoxetine which was given at a volume of 5 ml/kg. Neomycin was prepared as a solution in normal saline and injected into the tail vein 2 h prior to testing, that is, 1 h between the first and second administrations of the test drug. This approach has been reported to be effective in inhibiting endogenous brain PI metabolism for behavioral studies (67), although other approaches such as intracerebroventricular injection have also been used (68-69). Data were analyzed by one-way analysis of variance (ANOVA). Conclusions of mean differences were drawn when the calculated p-values were less than 0.05.

Brain Tissue Samples and Donor Demographics

The prefrontal cortex brain region was used, specifically Area BA 9 that is implicated in major depression. Fresh frozen human frontal cortex samples were obtained from the NICHD Brain and Tissue Bank at the University of Maryland Baltimore (UMB Bank). The UMB Bank was selected for tissue procurement because of their growing catalog of frozen brain samples from control and depression subjects, and the tissues are obtained through standardized dissection, handling, and preservation protocols. To enhance homogeneity of samples, each tissue sample was minced and the pieces mixed and then aliquots taken for downstream analysis. A set of 28 diagnosed depression cases having acceptable medical history documentation was matched to a set of unaffected controls based on sex, age (+/−3 yr), ethnicity, postmortem interval (PMI, +/−6 hr), and storage duration (+/−6 mo). Among the 28 pairs of control (Con) and depression (Dep) subjects that were matched, each diagnostic group consisted of 13 males and 15 females, 5 African and 23 Caucasian. The mean age (±SD) of the groups was Con 34.3±17.6 and Dep 34.4±17.3 yr, and the average PMI (±SD) is Con 17.8±7.2 and Dep 17.0±6.4 hr. Among the Dep subjects, 18 had a medical history or autopsy record of antidepressant medication use, and 6 had a record of other medications which belong to pharmacologic classes not known to significantly affect CDP-diacylglycerol levels. Samples were coded to remain blind to the experimenter until data collection had completed.

Collection of Blood and RNA Extraction

Blood was collected from three healthy volunteers by finger prick using a Actilance Universal contact-activated lancet (HTL-STREFA Inc., Marietta, Ga.). Three drops of blood were transferred by capillary tube into EDTA-treated blood collection microtubes at room temperature and the tube shaken to mix the blood with anticoagulant and prevent clotting.

RNA and Protein Extraction

Approximately 100 mg of each brain tissue sample was homogenized and aliquots taken for RNA and protein extraction. In the case of the blood sample, a 100-µl aliquot of whole blood was used. Total RNA was extracted using SurePrep RNA purification kit (Fisher Scientific) using the manufacturer's protocol that is based on elution from RNA-binding columns.

CDS protein was extracted from the same sample used for extraction of RNA. The flowthrough from the RNA binding column together with the first rinse of the column were collected into centrifuge tubes and spun at 3000×g for 20 min to remove the red blood cells. The supernatant containing the blood plasma was collected as the crude protein extract.

Quantitative Realtime PCR for CDS1 and CDS2 mRNA Levels

The purified RNA sample extracted from brain or blood was quantified using Nanodrop 2000c spectrophotometer (Thermo Scientific) and the purity was checked by the 260/280 absorbance ratio. Quantitative RT-PCR analysis was carried out using 100 ng of purified RNA. Verso One-step qRT-PCR master mix (Thermo Fischer Scientific) and Solaris gene expression assay system (ThermoScientific Dharmacon) were used. The mRNA expression levels of CDS1, CDS2 and GAPDH were measured by qRT-PCR. The primers specific for these transcripts were, for CDS1-Forward primer: 5'-CTGGTTTATCTTCAAGGTGGAAA-3' (SEQ ID NO: 1), Reverse primer: 5'-TTCACTTGGAT-GCCCAGAAC-3' (SEQ ID NO: 2), Probe: 5'-CTTCATGCTGATGCTTCTTG-3' (SEQ ID NO: 3); for CDS2-Forward primer: 5'-CCTATTTGAAGGAAT-GATCTGGTTC-3' (SEQ ID NO: 4), Reverse primer: 5'-GGCCATGATGTCATTACAG-3' (SEQ ID NO: 5), Probe: 5'-CCCATATCTTGTGTGATCT-3' (SEQ ID NO: 6) and for GAPDH-Forward primer: 5'-GCCCTCAAGAT-CATCAGCAATG-3' (SEQ ID NO: 7), Reverse primer: 5'-CTTCCACGATACCAAAGTTGTC-3' (SEQ ID NO: 8) and probe: 5'-GCCAAGGTCATCCATGA-3' (SEQ ID NO: 9). The cycling conditions in the Eppendorff Mastercycler were 50° C. for 15 min, 95° C. for 15 min, and 40 cycles of 95° C. for 15 sec and 60° C. for 60 sec. Cycle threshold (Ct) values were obtained from the Mastercycler software and the relative expression values of CDS1 and CDS2 were calculated by delta-Ct using GAPDH as the reference gene.

Measurement of CDS1 and CDS2 Protein Levels

Figure 1A:
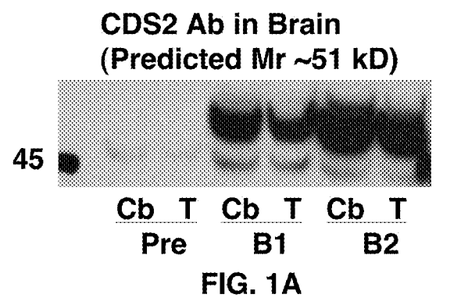
FIGS. 1A-1C shows High and specific immunoreactivity of rabbit antibodies raised against the human CDS1 and CDS2 proteins using epitopes designed to cross-react with the rat CDS1 and CDS2, respectively. Rabbit anti-human/rat preimmune sera (Pre), first-bleed (B1) second-bleed (B2) and protein A-purified second-bleed (B2p) antisera were tested against protein extracts from rat cerebellum (Cb) or testes (T) or against extracts of HEK293 cells transfected with empty (H0), CDS1 (H1) or CDS2 (H2) plasmids. Antisera (B1 or B2) from cds2-immunized rabbits showed strong reactions with cerebellar or testicular protein extracts (FIG. 1A), while antisera (B2) from cds1-immunized rabbits showed high reactivity with testicular extracts and moderate reactivity with cerebellar extracts (FIG. 1B). Wild type and cds2-transfected HEK293 cells showed substantial reaction to protein A-purified cds1 antibodies, indicating the presence of wild type cds1 in these cells (FIG. 1C). Cells transfected with cds1, however, gave overwhelming reactivity to the cds1 antibody. Importantly, the cds1 and cds2 antibody reactivities were located at approximately the expected Mr of 65 kD and 51 kD, respectively.
Figure 1B:
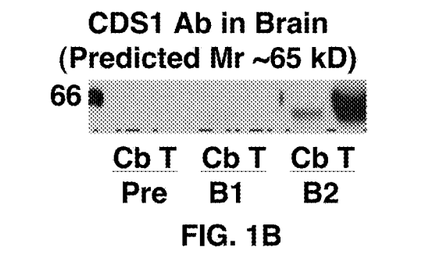
Figure 1C:
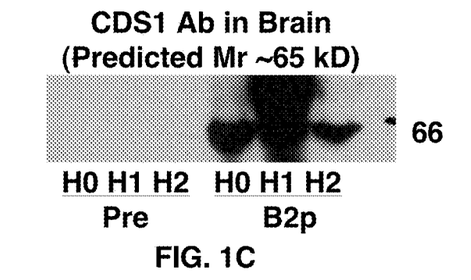

Protein extract was mixed and an aliquot used to measure total protein content using the Bradford assay. Aliquots containing 5, 10, or 20-µg protein were then taken for dot blot analysis; the lower protein samples yielded more consistent data for cds2 while the higher protein samples worked best for cds1 seeing as cds2 was expressed at much higher levels than cds1. The sample was diluted with PBS, transferred into the reservoir of a Bio-Dot SF microfiltration apparatus (Bio-Rad), and filtered under steady pressure onto a nitrocellulose blotting membrane. The protein-blotted membrane was blocked with 5% fat-free dry milk in PBS containing 0.1% Tween 20 (PBST) and incubated overnight at 4oC with CDS1 antibody (1:1000 dilution) or CDS2 antibody (1:1000 dilution) or beta-actin antibody. The CDS1 and CDS2 antibodies used were generated from peptide epitopes of the human CDS1 (amino acid sequence: CDDRYGDLDSRTDSDI (SEQ ID NO: 10)) and CDS2 (amino acid sequence: CDKESESEAKVDGETA (SEQ ID NO: 11)), respectively. The reactivity and specificity of the antibodies were first validated before use (see results in FIG. 1). Membranes were washed 3× with PBST and then incubated with HRP-conjugated secondary antibodies (1:10,000) for 1 h at room temperature. Visualization was performed by use of Amersham ECL plus Western blotting detection system (GE healthcare, Buckinghamshire, UK). Chemiluminescence images were analyzed by densitometry using the Kodak ImageStation 4000 MM. CDS1 and CDS2 densitometric values were normalized against beta-actin and the data are expressed as relative densitometric units×$10^3$.

Generally, GAPDH and/or beta-actin were used as standards. Precautions including assessment of RNA quality, parallel analysis of control and depression samples, and triplicate analyses of each sample were applied as in previous studies of other postmortem brain transcripts (73-75).

Data Analysis

Data from the various experiments were normalized relative to the respective control or basal measurements, and then pooled for analysis. Data were tested by an appropriate analysis of variance (ANOVA) using SPSS software (SPSS, Chicago, Ill., USA). Where warranted, the ANOVAs were followed by post hoc analyses using the Dunnett test to compare various treatment means to their respective controls. Statistical comparisons were considered significant at $p < 0.05$ or better.

After data collection, sample codes were broken to reveal the diagnostic category of each sample and permit data analysis. Data were collated and managed in SPSS software (SPSS Inc, Chicago, Ill.). Quantitative data for each dependent variable (CDS1 mRNA, CDS1 protein, CDS2 mRNA, CDS2 protein) were subjected to an independent samples (IS) t-test to compare the control versus depression measurements for each tissue. Further, each analyte was examined by analysis of covariance to exclude (or account for) the possible contributions of the various demographic factors (e.g., sex, race, pmi) to the study variables. Analyses with subcategories of independent variables, such as diagnosis and antidepressant exposure (e.g., Con, Dep-NoAD, Dep+AD) were also explored. For all analyses, comparisons between mean values were considered statistically significant at $p < 0.05$ or better.

EXAMPLE 2

Chemically Diverse Antidepressant Agents Increase CDP-Diacylglycerol Production

Diacylglycerol released from phospholipid breakdown is normally rapidly phosphorylated to produce phosphatidic acid. In the presence of [$^3$H]cytidine-labeled CTP, however, the phosphatidic acid is converted to radiolabeled CDP-DG, which can be extracted and separated away from other labeled metabolites and subsequently quantified. Rat brain cerebrocortical, hippocampal, and striatal slices prelabeled with [$^3$H]cytidine were incubated with various concentrations of selected antidepressant agents in the presence of LiCl, and the yield of CDP-diacylglycerol analyzed. Data for each drug were separately analyzed before they were normalized and collated together for graphical presentation as shown.

The classical antidepressants imipramine and desipramine, the selective serotonin reuptake inhibitors fluoxetine and paroxetine and the atypical agents maprotiline and nomifensine each significantly and dose-dependently enhanced the accumulation of [$^3$H]CDP-DG in rat hippocampal, prefrontal cortical, and striatal slices. While concentrations ranging from 0.1 to 1000 µM were tested, only those concentrations lying between the minimal that gave statistically significant effects for any agent (1-3 µM) and the maximally effective concentrations (100-500 µM) are shown. Statistically significant effects were obtained at concentrations as low as 3-10 µM in the hippocampus or prefrontal cortex, while maximal effects were achieved at the 100 µM concentration of fluoxetine or 300 µM concentrations of most other agents. For all agents, test concentrations greater than 300 µM resulted in CDP-DG effects that were either statistically similar to, or significantly lower than, the effects observed at 100 µM for fluoxetine or 300 µM for the other agents. This reduction in response with increasing concentration after attaining maximal responses was more apparent with the SSRIs, fluoxetine and paroxetine, than with the tricyclic agents.

Similar to the effects exhibited by the classical antidepressant agents, the monoamine oxidase inhibitors (MAOIs), phenelzine and hydralazine, produced robust effects on CDP-DG accumulation in frontal cortex slices, while tranylcypromine had statistically significant but modest effects. While the effects of phenelzine achieved significance at 1 µM (Dunnett's, p<0.01), those of hydralazine became significant at the 10 µM and higher concentrations.

Also, a range of other psychotropic compounds were tested to estimate the extent to which the CDP-DG response may characterize compounds with antidepressive activity. No significant effects or concentration-related effects on CDP-diacylglycerol accumulation in rat cerebrocortical slices were observed with the MAOIs pargyline, selegiline, or quinacrine, the antipsychotics chloropromazine, haloperidol, sulpiride, and flupenthioxol and the anticonvulsants or anxiotytics phenobarbital, phenytoin, diazepam, nitrazepam, benztropine, phenylephrine, chlordiazepoxide, and hydroxylamine. Agents were tested at multiple concentrations ranging from 0.1-300 µM. Data from up to three separate runs were normalized and pooled for analysis by One-Way ANOVA.

Among the brain regions, the hippocampus appeared to be more sensitive, i.e., greater response magnitudes at lower concentrations, whereas the striatum gave slightly more robust, i.e., maximally attained, effects. The drug responses were statistically dose-dependent for all effective agents in each tissue, but there were noticeable differences in potency or efficacy among the compounds as shown in the data. Thus, diverse antidepressant agents can acutely induce CDP-DG synthesis in depression-relevant regions of the rat brain.

EXAMPLE 3

Antidepressant-Induced CDP-Diacylqlycerol Formation Translates into Increased Phosphoinositide Synthesis To test if the antidepressant-enhanced CDP-DG translates into increased synthesis of the PIs, brain slice preparations were labeled with [$^3$H] inositol and incubated in the presence of various antidepressant agents. Results of the subsequent uptake and conversion of [$^3$H] inositol into inositol phospholipids are provided herein. Imipramine, desipramine, fluoxetine, paroxetine, and maprotiline each significantly increased [$^3$H]inositol labeling of PIs in the tested brain regions. MAOIs that were effective in inducing CDP-DG production also showed enhanced effects on PI resynthesis, whereas other MAOIs that were ineffective on CDP-DG were equally ineffective in increasing PI resynthesis. Thus, the increased mobilization or recapture of CDP-DG by the antidepressant agents translates into increased regeneration of PI signaling substrates.

EXAMPLE 4

Antidepressant Agents Generally Enhance Inositol Phosphate Accumulation

To test if resynthesized PIs might contribute to enhanced IP accumulation, agents tested for effects on CDP-DG were also tested in a standard IP assay. Across a concentration range of 3-300 µM, imipramine, desipramine, fluoxetine, paroxetine, and maprotiline significantly and dose-dependently stimulated the accumulation of IPs in each brain region. Significant drug effects were generally evident at concentrations of 3-10 µM, while maximal effects were observed at 100-300 µM. With imipramine tested in the hippocampus and striatum as the only possible exceptions, test concentrations greater than 300 µM resulted in IP effects that were either statistically similar to, or significantly lower than, the effects observed at the corresponding 300 µM concentration. In general, drug concentrations greater than 300-500 µM were associated with IP levels that were significantly lower than effects at 100-300 µM concentrations, possibly reflecting toxicity from excessive stimulation.

EXAMPLE 5

Antidepressant-Induced CDP-Diacylglycerol Formation Partially Depends on Phosphoinositide Hydrolysis Phosphoinositide hydrolysis is a major source, but not the only possible source, of diacylglycerol in the cell. To estimate the extent to which antidepressant-enhanced CDP-DG may derive from PI breakdown, PI hydrolysis was blocked and the consequent effects on the ability of antidepressant agents to induce CDP-DG accumulation were measured. First, the effects of the general PI metabolism inhibitor, neomycin, was tested against the maximally effective concentrations of the selected antidepressant agents. Neomycin concentration-dependently blocked the effects of imipramine, desipramine, fluoxetine, paroxetine, maprotiline, or nomifensine on CDP-DG production, PI resynthesis or IP accumulation in hippocampal or prefrontal cortical brain slices. Increasing concentrations of neomycin produced complete blockade of both CDP-DG and PI responses.

Next, the effects of the selective PLC inhibitor, U73122, were tested on the drug responses. U73122 by itself did not significantly alter basal CDP-DG production or IP accumulation, although a slight increase in IP was consistently noted. At concentrations ranging from 0.1 to 10 µM, U73122 significantly reduced, but was unable to completely block, antidepressant drug effects on CDP-DG production. Conversely, the PLC inhibitor completely blocked IP stimulation by 100 µM fluoxetine or 300 µM concentrations of imipramine, paroxetine, maprotiline, or nomifensine in hippocampal or cortical slices.

To validate the effects of U73122, the compound was tested against the action of SKF38393, a $D_1$ receptor agonist that is known to induce PI hydrolysis in these brain tissues (57,70). SKF38393-induced IP accumulation was blocked by U73122 with similar efficacies to the inhibition of the antidepressant responses. Moreover, U73123, an analog of U73122 that is ineffective in blocking PLC activity, was without effect on any of the CDP-DG or IP responses (data not shown). The effects of the SSRIs fluoxetine and paroxetine were more sensitive to inhibition by U73122 than the effects of the tricyclic agents.

EXAMPLE 6

Lithium is not Required for Antidepressant Drug Effects on CDP-Diacylglycerol

These experiments were designed to compare antidepressant drug effects on the IP and diacylglycerol arms of the inositol cycle. Thus, it was necessary to include LiCl in all test incubations. $Li^+$ is needed to block inositol monophosphatase and thereby enable the accumulation of released IPs to measurable levels. Selected antidepressant agents were tested for effects on CDP-DG in the absence or presence of 5 mM LiCl to determine if $Li^+$ must be present to demonstrate antidepressant drug effects on CDP-DG. LiCl did not significantly enhance or inhibit antidepressant drug-induced CDP-DG production, implying that the presence of $Li^+$ is not necessary to demonstrate the enhancing effects of antidepressant agents on CDP-DG production.

EXAMPLE 7

Antidepressants Elicit Relatively Greater Stimulation of CDP-Diacylglycerol Production than IP Formation To determine if antidepressant agents exert differential effects on CDP-DG production compared to PI hydrolysis, the ratios of CDP-DG production relative to the IPs (CDP-DG/IP ratio) in corresponding treatment conditions were examined. The ratios were calculated from the data herein and the results are provided. With each antidepressant agent, the CDP-DG/IP ratios increased significantly with increasing drug concentrations. This was true for different classes of drugs, including the MAOIs phenelzine and hydralazine.

EXAMPLE 8

Monoamine Receptor Agonists Exert Divergent Effects on CDP-Diacylglycerol

To determine which, if any, of the endogenous monoaminergic systems may show similar profiles of CDP-DG/IP effects, agonists that act directly at PLC-coupled monoaminergic receptors: α-methylserotonin ($5HT_2$ serotonergic), carbachol (muscarinic cholinergic), SKF38393 ($D_1$-like dopaminergic), and phenylephrine (alpha-adrenergic) were used. Corresponding CDP-DG ratios were calculated as for the antidepressant agents. As shown, α-methylserotonin, carbachol, phenylephrine or SKF38393 significantly increased IP accumulation and CDP-DG production in frontal cortex or hippocampal tissues. Carbachol failed to increase PI synthesis, SKF38393 significantly enhanced PI synthesis, while the other two agents had significant but relatively small effects on PI. The ratios of CDP-DG production relative to IP accumulation are provided herein.

With both carbachol and phenylephrine, there was a dramatic decrease in the CDP-DG/IP ratio. While the ratio did not decrease as much for α-methylserotonin, there was no concentration-related increase either. Conversely, SKF38393 increased CDP-DG/IP ratios significantly and in a manner similar to the antidepressants. Indeed, even the ratios of CDP-DG relative to PIs or the combination of both inositol derivatives (CDP-DG/IP&PI) were significantly enhanced. Thus, agonists at the direct PLC-coupled monoamine receptors showed parallel and corresponding changes between CDP-DG and the inositides, except for the dopamine agonist which, like the antidepressants, induced proportionately greater production of CDP-DG relative to inositide derivatives.

EXAMPLE 9

Antidepressants Enhance Methylserotonin-Stimulated IP Accumulation in [$^3$H]Inositol-Prelabeled Tissues Brain hippocampal, frontal cortical, and striatal slices were labeled with [$^3$H]inositol in the presence of various concentrations of selected antidepressant agents and, after washing the tissues, aliquots of the slices were incubated with indicated concentrations of α-methylserotonin for an additional 60 min. The levels of accumulated [$^3$H]IPs, assayed by Dowex ion exchange chromatography, are provided herein for the hippocampus, frontal cortex and striatum. By itself, α-Me5HT induced significant increases in IP accumulation; these effects, however, were significantly enhanced in tissues that had been prelabeled with tritiated inositol in the presence of the antidepressant agent imipramine, desipramine, fluoxetine paroxetine, and maprotiline.

The effects of α-methylserotonin were further concentration-dependently enhanced in hippocampal tissues that were prelabeled in the presence of each antidepressant agent ($p<0.001$), in frontal cortex tissues prelabeled in the presence of imipramine and desipramine ($p<0.02$) and the other agents ($p<0.001$ each), and in striatal tissues prelabeled in the presence of fluoxetine, paroxetine, and maprotiline ($p<0.001$). α-Methylserotonin effects, however, were not significantly enhanced in striatal tissues prelabeled in the presence of imipramine or desipramine ($p>0.05$). In all tissues where there were significant effects of antidepressant agents, there were significant interactions between the concentrations of antidepressant agent used and the concentrations of the 5HT2 agonist tested. Hence, the concentration-related effects of α-methylserotonin were maintained, but accentuated, in tissues prelabeled under the influence of the antidepressant agents.

The zero α-methylserotonin data represent tissues that had been prelabeled in the presence of the indicated concentrations of antidepressant agents, further incubated alongside the α-methylserotonin-tested tissues, and subsequently analyzed for the basal content of inositol phosphates. In these tissues that did not receive α-methylserotonin, there were generally increased levels of IPs with increasing concentrations of the antidepressant agents.

Thus, mere prelabeling of the tissues in the presence of antidepressant agents led to increased accumulations of inositol phosphates even in the absence of exogenous 5HT2 receptor stimulation. These effects were statistically significant for all agents at at least their highest tested concentrations in each brain region (ANOVA, $p<0.001$ in each case). The net effects of the combined exposure to antidepressant and α-methylserotonin were not significantly different from the sum of the separate effects of antidepressant and α-methylserotonin, thus suggesting an additive mechanism of interaction between AD and α-methylserotonin treatments.

EXAMPLE 10

Effects of 5HT2 Receptor Blockade on Drug-Induced IP Accumulation

To examine the extent to which the enhancing effects of antidepressant agents on inositol phosphate accumulation were dependent on postsynaptic 5HT2 receptor stimulation, each antidepressant was challenged with a range of concentrations of the 5HT2 receptor-selective antagonist, LY53857 (71-72). The antagonist was added after the prelabeling phase, but 15 min prior to the addition of α-methylserotonin to the incubating slices. LY53857 did not significantly alter the basal levels of IPs or PIs, but increased CDP-diacylglycerol by 20% at the 0.1 μM concentration. The 5HT2 antagonist completely blocked the IP responses to each of the AD agents ($p<0.001$ in each case). PI labeling and CDP-diacylglycerol responses were statistically significantly inhibited ($p<0.05$ or better) for all drugs; however, only the inhibition of PI labeling induced by fluoxetine and paroxetine was substantial.

While the results shown are for the hippocampus, similar observations were made in frontal cortex tissues. With regard to antidepressant-enhanced phosphatidylinositol resynthesis, 5HT2 receptor blockade significantly inhibited the effects of the SSRIs fluoxetine and paroxetine, but the effects of the tricyclic agents imipramine and desipramine or those of maprotiline were only partially, though significantly, reduced. Moreover, antidepressant drug effects on CDP-diacylglycerol were only minimally, though statistically significantly, inhibited by the 5HT2 antagonist. Thus, antidepressant-facilitated release of IP second messengers requires intact 5HT2 receptor function, whereas antidepressant drug effects on CDP-diacylglycerol or phosphatidylinositol labeling may facilitate, but not depend on, postsynaptic 5HT2 receptor signaling.

EXAMPLE 11

Effects of Blocking Endogenous PI Metabolism on Antidepressant-Induced Behavioral Effects in the Forced Swim Test Imipramine was first tested by both the conventional regimen using one acclimation with three-point drug administration and the current modification using two acclimations with two-point drug administration, of the forced swim test. Either method produced significant dose-related effects for imipramine on immobility behavior ($p<0.001$ for each dataset). Immobility times were slightly higher in the modified test than in the conventional test ($p<0.05$). Most significantly, the variability in the data was much reduced in animals that underwent two acclimation sessions; hence, the mean coefficient of variation was 2.6-fold lower in the modified test than in the conventional approach.

Following pretreatment with saline (controls) or neomycin, animals were subjected to the forced swim test in the presence or absence of selected antidepressant agents. Imipramine, fluoxetine, and maprotiline each induced significant and dose-dependent reductions of immobility times in the forced swim test, and these effects were completely reversed in animals that received neomycin pretreatments. Yet, neomycin by itself did not significantly alter basal immobility times in any of the experiments. SKF38393 was tested in the absence and presence of neomycin. SKF38393 significantly decreased immobility times similar to the effects of the clinical antidepressant agents and this action was blocked by neomycin. Apparently, the acute behavioral effects of the drugs in at least the forced swim test depend on intact functioning of brain PI systems.

EXAMPLE 12

Specific Immunoreactivity of Generated cds1 and cds2 Antibodies

Rabbit antibodies raised against human cds1 and cds2 peptides (identical in sequence to rat cds1 and cds2) respectively immunoreacted against the specific peptides, and detected the respective proteins in rat cerebellar or testicular tissue extracts (these tissues express high levels of cds1/cds2) (FIG. 1). HEK293 cells transfected with cds1 or cds2 plasmids showed high reactivity to the respective antisera in comparison with relatively weaker reactions of the antisera against untransfected HEK293 cells. Subcellular fractionation experiments showed highest reactivity to cds1 in the microsomal fraction while the highest reactivity to cds2 was present in the mitochondrial cellular fraction (rat data shown in FIG. 1 for cds1 reflect microsomal fraction and for cds2 the mitochondrial fraction, whereas human brain or blood samples were not fractionated).

EXAMPLE 13

CDS1 and CDS2 mRNA and Protein Levels in Postmortem Human Brain of Control and Depression Subjects Quantitative PCR analysis of cds1 and cds2 transcripts in medial prefrontal cortex samples of 28 matched pairs of control (Con) and depression (Dep) subjects were conducted. CDS protein levels were also analyzed by semiquantitative Western Blotting of triplicate tissue lysates from 16 pairs of qualified subjects. Statistical analyses yielded the following results:

CDS1 and CDS2 protein or mRNA expression levels were consistent with the Normal distribution for both the Con and Dep subjects (K-S test). On this basis, robust parametric approaches were used for inferential analysis of the data.

The mRNA levels of cds1 were significantly correlated with cds2 ($p<0.001$), as well as the cds1/cds2 ratio ($p<0.01$) when examined across all subjects or separately for each diagnostic group. This could reflect sample variability, in which case using the ratio data can correct for some of that variability, or it may suggest that cds1 and cds2 are co-regulated.

Expression levels of cds1 or cds2 mRNA or protein did not correlate with subject age (15-50 y) or postmortem interval (3-33 h). An Independent Samples (IS) t-test showed no significant differences in cds1 or cds2 mRNA levels when compared on sex (18 male v. 24 female) or race (8 African v. 34 caucasian), although the data trended toward lower cds1 (p=0.167) or cds2 (p=0.146) in the older group. Protein levels of cds1 appeared significantly higher in the African v. Caucasian subjects (p<0.05). With the possible exception of the race observations, the demographic factors may not play a significant role in determining the brain cortical levels of cds transcripts. This increases the strength and clinical significance of any associations that may be found between cds mRNA levels and a diagnosis of depression.

Figure 2A:
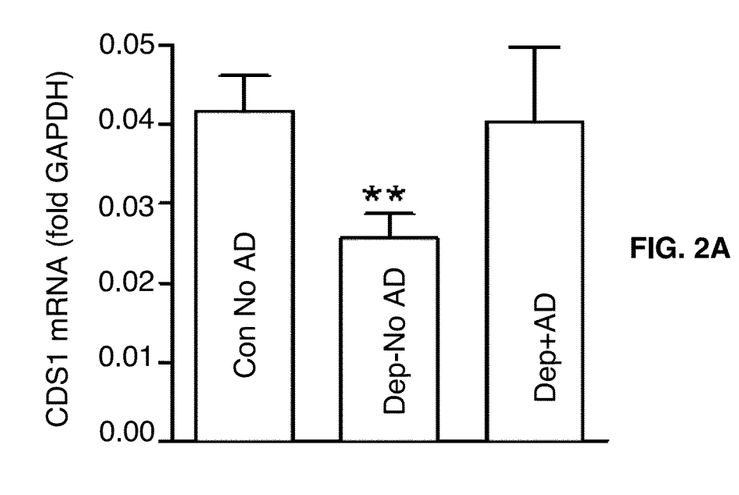
FIGS. 2A-2B show CDS1 mRNA (FIG. 2A) and protein levels (FIG. 2B) in postmortem frontal cortex Area BA9 samples from normal control (no depression or antidepressant (AD) drug exposure) and depression (Dep) subjects without (No-AD) or with AD (+AD) medication. Depression subjects showed significantly lower levels of CDS1 message and protein, while those depression subjects that had taken (any) antidepressant medication showed intermediate levels of CDS1 mRNA and protein.

Mean cds1 mRNA levels in the Dep group (0.0284±0.0037) were significantly lower than corresponding levels in the Con group (0.0417±0.0044) when compared by Paired Samples (PS) t-test (p<0.01) or IS t-test (P<0.03) (FIG. 2A). Similar results were obtained for cds1/cds2 ratio data. Mean expression levels of cds2 mRNA, however, were not significantly different between Con (0.2642±0.0251) and Dep (0.2447±0.0216) samples when compared by PS (p>0.226) or IS (P>0.561) t-tests.

Figure 2B:
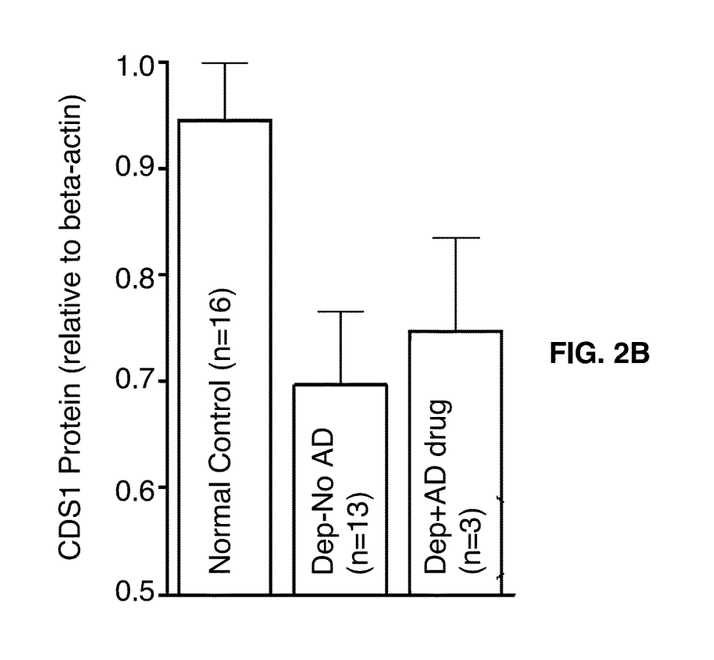

Similar to the cds1 mRNA results, mean cds1 protein levels were significantly lower in the Dep group (0.70612±0.058057) compared to the Con group (0.94494±0.059317) by IS t-test (p<0.007, N=16) (FIG. 2B). The finding that cds1 levels were significantly decreased in the Dep group implies that cds1, but not necessarily cds2, is a biosignature in depression.

EXAMPLE 14

Effects of Antidepressant Medication Use on cds1 mRNA and Protein Levels

Based on information from autopsy or medical history reports, subjects were identified who had been on antidepressant (AD) medication prior to death (history) or at death (autopsy). These subjects were then classified based on Diagnosis-AD medication as follows: Control subjects-No AD, Dep-Noncurrent AD, and Dep+Current AD. A One-Way ANOVA revealed significant main effects (p<0.03 for cds1mRNA; p<0.03 for cds1 protein; p<0.005 for cds1/cds2 mRNA ratio). Subsequent posthoc Dunnett analyses showed significant differences (p<0.02) between the higher mean cds1 mRNA values in Con-No AD subjects (0.0417±0.0044) and lower mean cds1 mRNA values in the Dep-Noncurrent AD group (0.0256±0.0031) (FIG. 2A). CDS ratio data gave similar conclusions, but with higher significance levels. The posthoc analyses for cds1 protein showed no significant differences between any pair of groups, possibly because of the low sample sizes involved (see graph); nevertheless, there were trends toward the direction of the mRNA data (FIG. 2B).

Interestingly, Dunnett analysis of the cds1 mRNA data indicated no difference between control subjects and depression subjects who were currently using antidepressant medications (mean=0.0403±0.0095; p>0.78). Antidepressant drugs in the current AD drug users may have "normalized" the decreased cds1 levels seen in nonmedicated depressed subjects.

EXAMPLE 15

CDS1 and CDS2 mRNA and Protein Levels in Circulating Peripheral Blood of Normal Human Volunteers Each subject was tested on five separate occasions and each sample drawn was tested in duplicate. The mean CDS1 values obtained in Replicate1 versus Replicate2 were 2.014±0.261 and 2.076±0.278 (N=5), while for CDS2 these values were 564.7±91.4 and 762.2±98.8 (N=5), respectively. There is no statistically significant difference between the CDS1 (p>0.68) or CDS2 (p>0.16) replicates, while there is a highly significant Pearson correlation between the replicate cds1 values (p<0.001), thus supporting the high reproducibility of the assay method.

Reproducibility of Analyte Measurements

Data obtained across the five test sessions were analyzed by Repeat Measures ANOVA which showed no significant difference in mean values across the experimental sessions for CDS1 (p>0.134) or CDS2 (p>0.494). Thus, for normal subjects, the assay is reproducible across test sessions and the cds values remain stable over this time period.

Relationship Between CDS1 and CDS2 Expression Levels

Mean levels of cds1 (2.045±0.259) and cds2 (663.5±67.7) (N=5) were significantly different (p<0.001), and their relative abundance corresponds well with the preceding observations in human postmortem brain tissues.

CDS1 Protein Expression

Mean cds1 protein expression was 2.132±0.089 relative to beta-actin protein levels. This method and the findings provide an overall indication of normal blood CDS1 (and cds2) expression in living human subjects. Both the mRNA and protein levels of cds1 were measured reproducibly in microliter aliquots of human blood samples. Overall, it is remarkable that such relatively high levels of cds1 mRNA and protein could be measured reproducibly in microliter samples (technically five drops) of whole human blood.

EXAMPLE 16

Discussion and Conclusion

The present invention found decreased expression levels of CDS1 but not necessarily CDS2 in a depression-relevant region of the frontal cortex from depressed subjects compared to normal controls. A well-correlated trend of increasing CDS1 expression was found in depression subjects that were on antidepressant medication around the time of death, implying that the drug treatments might have been working to restore the normal levels of CDS1 expression and/or activity. Furthermore, blockade of downstream CDP-diacylglycerol activity prevented the therapy-relevant behavioral effects of the antidepressant drugs. The data are noteworthy in establishing a reproducible assay for the quantification of CDS expression in relatively small amounts of whole human blood, thus hinting at the potential clinical applicability of the overall results.

The CDP-diacylglycerol (CDG)/CDP-diacylglycerol synthase (CDS) system is ubiquitous and plays unique roles in cellular function. The enzymatic activity of CDS exists as two protein isoforms, CDS1 and CDS2, either of which produces CDP-diacylglycerol, a nucleolipid. The nucleolipid products of CDS may have arachidonoyl or stearoyl derivatives at the C-1/C-2 position of the glycerol moiety. Studies in nonhuman species indicate that CDS1 produces primarily 2-arachidonoyl-[CDP-diacylglycerol] which is utilized for the production of phosphatidylinositol for downstream multipartite metabotropic signaling cascades; conversely, the primary products of CDS2 are comparatively saturated derivatives of CDP-diacylglycerol (e.g., 2-stearoly-[CDP-diacylglycerol]) that are utilized for the synthesis of phosphatidylglycerol and ultimately cardiolipin biosynthesis. It has been suggested that CDS1 is localized primarily to the endoplasmic reticulum, whereas CDS2 is localized primarily in mitochondria. These observations are consistent with the differential effects of depressive illness on CDS1 versus CDS2, and also hint at the possibility that separate functions may be found for CDS2 in physiological or pathological conditions such that drugs or diagnostics targeting CDS1 may not necessarily impact on the biological functions of CDS2.

The CDS/CDG model of depression or antidepressant drug mechanisms is the first to present a potentially unifying molecular explanation for the beneficial clinical effects of the wide variety of available AD medications. An upstream action at the level of CDG synthesis and signaling could potentially explain many previously observed effects of AD drugs via the downstream cascades that would be modulated by enhanced CDG: enhanced PI/PLC leading to PKC/CamK activation, or increased PI/PI3K leading to Akt/GSK3_ or mTOR regulation. For instance, PI is a key substrate for the PI3K signaling pathway. Earlier reports showed that PI3K signaling is relevant to the induction of neurogenesis or neuronal survival and plasticity. Recent reports demonstrated that the activity of PI3K and its downstream target, Akt, are compromised in postmortem brain tissues of depressed suicide victims (76-77). Further downstream, these systems crosstalk to regulate CREB phosphorylation and BDNF signaling—processes that have been implicated in neurogenesis and AD mechanisms.

Thus, it is conceivable that an early action of AD agents to enhance the mobilization of CDG could lead to coordinate effects on multiple signaling systems, which might then explain the various molecular and functional effects of the drugs. By the proposed CDS/CDG model, an AD agent would minimally possess the ability to enhance CDG production and/or increase synaptic levels of brain monoamine neurotransmitters: serotonin (which does not by itself increase CDG but robustly generates downstream second messengers from CDG-derived PI), norepinephrine (which modestly enhances CDG resynthesis as well as generate PI signaling messengers) or dopamine (which robustly induces CDG synthesis and moderately increases PI/PLC signaling). A clear advantage, of course, would exist for those agents that possess dual abilities to raise synaptic monoamines and increase CDG synthesis; this may explain why many clinically effective AD medications such as imipramine, desipramine, maprotiline, fluoxetine, paroxetine, and phenelzine generally have these dual properties. These are innovative ideas that could open a new path through the formidable task of exploring the causes and clinical course of depressive illness and its treatment. The present study focusing on the CDS enzymes has extended prior work with CDG, the enzyme product, revealing consistent modulations of the CDS/CDG system in human depression.

The present report establishes CDS (particularly CDS1) as a correlate of depressive illness, thus advancing the idea to apply the levels of CDS1 enzymatic activity, protein, messenger RNA, and/or gene polymorphisms in a person's blood or other tissue sample to determine the likelihood (decreasing cds1 levels with repeated sampling), presence/severity (critically low cds1 levels as compared to previous levels or normative standards), or improvement/relief (recovery of cds1 levels above critical functional points) of major depression in humans. The biomedical literature contains numerous examples of correlations between brain and blood molecular or neurochemical indices of depression. For example, imipramine binding levels in blood platelets correlate with imipramine binding levels in brain tissue. Therefore, demonstration of decreased CDS1 mRNA (and protein) in the brain will correlate with similar decreases in the blood. Thus, measurements of CDS1 levels (absolute or relative to cds2) in the blood should reproducibly index corresponding brain measures and therefore serve as a reliable index for the diagnosis and prognostication of major depression. Indeed, the ability of a drug or other treatment to enhance CDS activity (via increased expression, decreased inactivation, or enhanced enzyme activation) could become indicative of ultimate antidepressant efficacy.

Major depression is currently diagnosed, and its treatment monitored, by subjective personal interview. There is currently no objective molecular or biochemical diagnostic test for depression, nor is there a test that indicates the severity or improvement of the disorder. The present invention holds promise for the development of a series of tests that could signal susceptibility to depression (if functionally relevant polymorphisms are detected in the person's CDS1 gene), an impending episode of depression (if repeated assays show decreasing levels of CDS), the severity of existing depression (if the levels of CDS fall below critical levels), or efficacy of treatment (if repeated samplings show improving—increasing—levels of CDS). Levels of CDS may refer to the enzymatic activity of CDS, the protein concentration of CDS (measured by standard assays such as electrophoresis, ELISA, mass spectrometry, etc), the mRNA concentration of CDS (measured by standard procedures such as quantitative PCR), or the polymorphism status of the CDS1 gene (measured by relevant genotyping assays).

The following references are cited herein:
1. Waslick et al. (2002). In: Shaffer et al (eds). The many faces of depression in children and adolescents. Am. Psychiatric Pub., Inc.: Washington D.C. pp 1-29.
2. Costello et al. (2003). Arch Gen Psychiatry 60:837-844.
3. Hasin et al. (2005). Arch Gen Psychiatry 62:1097-1106.
4. Ciraulo et al. (2004). Clinical pharmacology and therapeutics of antidepressants. In: Ciraulo et al., (eds). Pharmacotherapy of depression. Humana Press: Totowa N.J. pp 33-119.
5. Taylor et al. (2005). Cell Signal 17:549-557.
6. Feighner J P (1999). J Clin Psychiatry 60:4-11.
7. Frazer A (2000). J Clin Psychiatry 61:25-30.
8. Gould T D, Manji H K (2002). J Psychosom Res 53:687-697.
9. Delgado P L (2004). J Clin Psychiatry 65:25-30.
10. De Vivo M, Maayani S (1986). J Pharmacol Exp Ther 238:248-253.
11. De Vivo M, Maayani S (1990). Biochem Pharmacol 40:1551-1558.
12. Dumuis et al. (1988). Mol Pharmacol 33:178-186.
13. Undie et al. (1994). J Neurochem 62:2045-2048.
14. Dwivedi et al. (2002). Neuropharmacology 43:1269-1279.
15. Fumagalli et al. (2005). J Neurochem 93:1551-1560.
16. Chen J, Rasenick M M (1995). J Pharmacol Exp Ther 275:509-517.
17. Hines L M, Tabakoff B (2005). Biol Psychiatry 58:955-962.
18. Odagaki et al. (2001). Brain Res 898:224-231.
19. Shimizu et al. (1996). J Pharmacol Exp Ther 279:1551-1558.
20. Qu et al. (2003). npp 28:1219-1226.
21. Nibuya et al. (1996). J Neurosci 16:2365-2372.
22. Yamada et al. (2003). J Neural Transm 110:671-680.
23. Butler P D, Barkai A I (1987). Adv Exp Med Biol 221:531-547.
24. Pandey et al. (1991a). Psychopharmacol Bull 27:255-261.
25. Fukuda et al. (1994). Neurochem Int 25:567-571.

26. Pacheco et al. (1996). Brain Res 723:37-45.
27. Pandey et al. (1991b). J Pharmacol Exp Ther 256:1010-1018.
28. Morishita S, Aoki S (2002). J Affect Disord 70:329-332.
29. Morishita et al. (1999). Psychiatry Clin Neurosci 53:11-15.
30. Mann et al. (1995). Br J Pharmacol 115:595-600.
31. Einat et al. (2003). J Neurosci 23: 7311-7316.
32. Shimizu et al. (1993). J Neurochem 60:595-601.
33. Cuellar-Quintero et al. (2001). Neuroreport 12:2195-2198.
34. Coppell et al. (2003). Neuropharmacology 44:903-910.
35. Saarelainen et al. (2003). J Neurosci 23:349-357.
36. Xu et al. (2003). NPP 28:53-62.
37. Wong et al. (1996). Biochem Biophys Res Commun 229:275-279.
38. Manev et al. (2001b). Eur J Pharmacol 420:R1-R2.
39. Santarelli et al. (2003). Science 301:805-809.
40. Malberg et al. (2000). J Neurosci 20:9104-9110.
41. Manev et al. (2001a). Eur J Pharmacol 411:67-70.
42. Dong J, Blier P (2001). Psychopharmacology (Berl) 155:52-57.
43. Lesch K P, Manji H K (1992). Biol Psychiatry 32:549-579.
44. Drigues et al. (2003). J Neural Transm 110:1413-1436.
45. Landgrebe et al. (2002). J Psychiatr Res 36:119-129.
46. Palotas et al. (2004). Int J Neuropsychopharmacol 7:401-413.
47. Coupland et al. (2005). Biol Psychiatry 57:1526-1534.
48. Barkai et al. (1978). Biol Psychiatry 13:65-72.
49. Einat et al. (2001). Behav Brain Res 118:77-83.
50. Einat et al. (1999). Psychopharmacology (Berl) 144:158-162.
51. Levine J (1997). Eur Neuropsychopharmacol 7:147-155.
52. Manji H K, Chen G (2000). Curr Psychiatry Rep 2:479-489.
53. Sarri et al. (1995). Jour. of Pharmacology and Exp. Therapeutics 272:77-84.
54. Claro et al. (1993). J Neurochem 60:2078-2086.
55. Zhang et al. (2005). Neurosci Lett. 2005 Jul. 1-8; 382(1-2):134-8.
56. Watts et al. (1993). Eur J Pharmacol. 242(2):165-72.
57. Undie A S, Friedman E (1990). J Pharmacol Exp Ther 253:987-992.
58. Undie A S (1999). Brain Res 816:286-294.
59. Panchalingam S, Undie A S (2001). Neuropharmacology 40:826-837.
60. Godfrey P P (1989). Biochem J 258:621-624.
61. Undie A S, Friedman E (1992). Eur J Pharmacol 226: 297-302.
62. Stubbs E B, Jr. (1993). J Neurochem 60:1292-1299.
63. Billah M M, Michell R H (1978). Biochem Soc Trans 6:1033-1035.
64. Detke et al. (1995) Psychopharmacology (Berl) 121:66-72.
65. Porsolt et al. (1977) Arch Int Pharmacodyn Ther 229: 327-336.
66. Porsolt et al. (1978) Eur J Pharmacol 47:379-391.
67. Golding E M, Vink R (1994) Brain Res 668:46-53.
68. Coderre T J (1992) Neurosci Lett 140181-184.
69. Yamada et al. (1994) Neurosci Lett 165:191-194.
70. Undie et al. (1994) J Neurochem 62:2045-2048.
71. Engleman et al. (1992) Neurochem Res 17:483-488.
72. Hingtgen et al. (1985) Biol Psychiatry 20:592-597.
73. Koh et al. (2003) Proc Natl Acad Sci USA. 100:313-317.
74. Koh et al. (2003) Arch Gen Psychiatry. 60:311-319.
75. Bai et al. (2004) Biol Psychiatry. 56:427-440.
76. Hsiung et al. (2003) J Neurochem. 87:182-194.
77. Karege et al. (2011) Neuropsychobiology. 63:224-231.

Any publications mentioned in this specification are indicative of the levels of those skilled in the art to which the invention pertains. Further, these publications are incorporated by reference herein to the same extent as if each individual publication was specifically and individually incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of assessing and monitoring a depressive disorder in a test subject, comprising:
   obtaining a sample from the test subject and from a control subject;
   measuring an expression level of a CDP-diacylglycerol synthase 1 enzyme and of a CDP-diacylglycerol synthase 2 enzyme in the test sample and in the control sample;
   determining a ratio of the expression levels of the CDP-diacylglycerol synthase 1 enzyme to the CDP-diacylglycerol synthase 2 enzyme in the test sample and in the control sample;
   comparing the ratio of the expression levels in the test sample to the ratio of the expression levels in the control sample subject;
   assessing the test subject as having the depressive disorder when a statistically lower ratio is present in the test sample compared to the control sample; and
   monitoring said ratio in the test subject after an administration of an antidepressant drug to the test subject.

2. The method of claim 1, wherein the ratio of expression levels of the CDP-diacylglycerol synthase 1 enzyme to the CDP-diacylglycerol synthase 2 enzyme is determined by measuring a ratio of a CDP-diacylglycerol synthase 1 mRNA to a CDP-diacylglycerol synthase 2 mRNA.

3. The method of claim 1, wherein the sample is blood, brain tissue, testis tissue, eye tissue or smooth muscle tissue.

4. The method of claim 1, wherein the depressive disorder is major depression, unipolar depression, bipolar depression, reactive depression, endogenous depression, or dysthymic disorder.

5. The method of claim 1, wherein said test subject is assessed as having a depressive disorder when the ratio of the CDP-diacylglycerol synthase 1 mRNA to the CDP-diacylglycerol synthase 2 mRNA is about 73% or lower than the ratio of a CDP-diacylglycerol synthase 1 mRNA to the CDP-diacylglycerol synthase 2 mRNA in the control subject.

6. The method of claim 1, wherein the antidepressant drug is a tricyclic antidepressant, a selective serotonin reuptake inhibitor, an atypical antidepressant or a synthetic antidepressant compound that increases the ratio of the expression levels of the CDP-diacylglycerol synthase 1 enzyme to the CDP-diacylglycerol synthase 2 enzyme in a depression-relevant brain tissue or blood platelets.

7. The method of claim 6, wherein the tricyclic antidepressant is desipramine or imipramine and the selective serotonin reuptake inhibitor is fluoxetine or paroxetine.

8. The method of claim 1, wherein during monitoring of the test subject, a statistically higher ratio of expression levels after administration of the antidepressant drug indicates that the antidepressant drug has therapeutic efficacy for the subject.

* * * * *